(12) United States Patent
Wright et al.

(10) Patent No.: US 6,789,538 B2
(45) Date of Patent: Sep. 14, 2004

(54) RESCUE DEVICE AND KIT AND METHOD OF USING SAME

(75) Inventors: Clifford A. Wright, San Diego, CA (US); Kion Guold, San Diego, CA (US)

(73) Assignee: Medical Device Group, Inc.

( * ) Notice: Subject to any disclaimer, the term of this patent is extended or adjusted under 35 U.S.C. 154(b) by 0 days.

(21) Appl. No.: 10/305,528

(22) Filed: Nov. 27, 2002

(65) Prior Publication Data

US 2004/0099273 A1 May 27, 2004

(51) Int. Cl.$^7$ ............................................. A61M 16/00
(52) U.S. Cl. ............................ 128/200.26; 128/201.18; 128/207.14; 128/207.18
(58) Field of Search ..................... 128/200.26, 201.18, 128/207.14, 207.15, 207.18, 207.29

(56) References Cited

U.S. PATENT DOCUMENTS

| | | | | | |
|---|---|---|---|---|---|
| 384,777 | A | * | 6/1888 | Ochs ..................... | 128/200.21 |
| 3,039,469 | A | * | 6/1962 | Fountain ................ | 128/200.26 |
| 3,046,978 | A | * | 7/1962 | Lea ........................ | 128/205.13 |
| 3,088,466 | A | * | 5/1963 | Nichols ................. | 128/200.26 |
| 3,538,918 | A | * | 11/1970 | Hofstra et al. .......... | 128/200.26 |
| 3,809,079 | A | * | 5/1974 | Buttaravoli ............ | 128/206.24 |
| 3,814,103 | A | * | 6/1974 | Fettel et al. ........... | 128/207.18 |
| 3,964,488 | A | * | 6/1976 | Ring et al. ............. | 128/207.14 |
| 4,273,124 | A | * | 6/1981 | Zimmerman ........... | 128/207.18 |
| 4,449,526 | A | * | 5/1984 | Elam ..................... | 128/206.21 |
| 4,539,985 | A | * | 9/1985 | Magrath ................ | 128/205.13 |
| 4,821,715 | A | * | 4/1989 | Downing ............... | 128/207.18 |
| 4,825,861 | A | * | 5/1989 | Koss ..................... | 128/207.14 |
| 4,938,746 | A | * | 7/1990 | Etheredge et al. .......... | 604/265 |
| 4,949,716 | A | * | 8/1990 | Chenoweth ............ | 128/207.14 |
| 5,507,279 | A | * | 4/1996 | Fortune et al. ......... | 128/200.26 |
| 5,562,078 | A | * | 10/1996 | Dzwonkiewicz ....... | 128/207.18 |
| 5,762,063 | A | * | 6/1998 | Coates et al. .......... | 128/205.13 |
| 6,062,219 | A | * | 5/2000 | Lurie et al. ............ | 128/205.24 |
| 6,098,617 | A | | 8/2000 | Connell | |
| 6,098,621 | A | * | 8/2000 | Esnouf .................. | 128/205.13 |
| 6,378,523 | B1 | | 4/2002 | Christopher | |

OTHER PUBLICATIONS

"The Modified Nasal Trumpet Maneuver" by Charles Beattie, Anesth Analg 2002; 94: pp. 467–469: Published Feb. 2002.

"The Modified Nasal Trumpet: New Use for an Old Device", by Samuel Metz, Society for Technology, Anesthesia, Jan. 2002 Annual Meeting http://www.anestech.org/publications/Annual 2002/metz.html.

\* cited by examiner

*Primary Examiner*—Aaron J. Lewis
(74) *Attorney, Agent, or Firm*—Jerry R. Potts

(57) ABSTRACT

A rescue device and kit for ventilating a patient incapable of normal ventilation or intubation techniques includes a single-lumen nasopharyngeal nasal trumpet having a beveled shaped opening at its distal end and a flared proximal end. An eye opening is disposed slightly proximal to the beveled shaped opening and an air delivery extension tube is secured within the single-lumen opening at the flared proximal end of the nasal trumpet. The distal end of the extension tube secured within the nasal trumpet cooperates with the flared proximal end of the nasal trumpet to provide a soft non-tissue irritating nose plug when the nasal trumpet is fully inserted into a nostril opening of the patient. The kit further includes a tube of lubricant, an air bag, and a soft nose plug for blocking the other nostril opening of the patient during the novel rescue process. The ventilation rescue method includes providing a single-lumen nasopharyngeal nasal trumpet having a flared proximal end and a beveled shaped opening at its distal end with an eye opening disposed slightly proximal to its distal end and an air delivery extension tube secured within its flared proximal end opening. A medical practitioner using the nasal trumpet proceeds ventilating a patient by lubricating the nasal trumpet, inserting the trumpet by its distal bevel end into a single nostril of a distressed patient until the distal end occupies the periglottic space of the patient; attaching an air bag to the proximal end of the extension tube and then occluding the other nostril of the patient with the nose plug.

17 Claims, 4 Drawing Sheets

RESCUE DEVICE AND KIT AND METHOD OF USING SAME

FIELD OF THE INVENTION

The present invention pertains to a rescue device and kit and more particularly, to a nasopharyngeal airway device and kit for the delivery of positive-pressure ventilation to a patient when normal ventilation and intubation techniques are ineffective.

BACKGROUND OF THE INVENTION

During ventilation and intubation procedures medical personnel many times encounter conditions where a patient cannot be conventionally ventilated or intubated even after administration of muscle relaxants. In such cases, the normal protocol is to provide a surgical airway. Therefore, it would be highly desired to have a new and improved method, device and kit for establishing a nasopharyngeal airway without the need of providing a surgical airway.

SUMMARY OF THE INVENTION

In one preferred embodiment of the present invention, a rescue device and kit for ventilating a patient incapable of normal ventilation or intubation techniques includes a single-lumen nasopharyngeal nasal trumpet having a beveled shaped opening at its distal end and a flared proximal end. An eye opening is disposed slightly proximal to the beveled shaped opening and an air delivery extension tube is secured within the single-lumen opening at the flared proximal end of the nasal trumpet. The distal end of the extension tube secured within the nasal trumpet cooperates with the flared proximal end of the nasal trumpet to provide a soft non-issue irritating nose plug when the nasal trumpet is fully inserted into a nostril opening of the patient. The air delivery extension tube includes an endotracheal tube connector at its proximal end that is adapted to be connected in a fast convenient manner to an air delivery device. The extension tube has a sufficient length to space the air delivery device from the face of the patient to facilitate both patient comfort and easy in operating the air delivery device when it is attached at the proximal end of the air delivery extension tube. The kit further includes a tube of lubricant, an air bag, and a soft nose plug for blocking the other nostril opening of the patient during the novel rescue process.

The ventilation rescue method includes providing a single-lumen nasopharyngeal nasal trumpet having a flared proximal end and a beveled shaped opening at its distal end with an eye opening disposed slightly proximal to its distal end and an air delivery extension tube secured within its flared proximal end opening. A medical practitioner using the nasal trumpet proceeds ventilating a patient by lubricating the nasal trumpet, inserting the trumpet by its distal bevel end into a single nostril of a distressed patient until the distal end occupies the periglottic space of the patient; attaching an air bag to the proximal end of the extension tube and then occluding the other nostril of the patient with the nose plug. With the nasal trumpet so positioned the medical practitioner applies positive pressure to the air bag to distend the periglottic space of the patient and open the larynx thereby facilitating pulmonary exchange of air. The squeezing of the air bag is repeated in synchronization with the inspiratory phase allowing sufficient time for exhalation through the mouth of the patient.

BRIEF DESCRIPTION OF THE DRAWINGS

The above-mentioned features and steps of the invention and the manner of attaining them will become apparent, and the invention itself will be best understood by reference to the following description of the embodiments of the invention in conjunction with the accompanying drawings wherein.

DETAILED DESCRIPTION OF THE PREFERRED EMBODIMENT OF THE INVENTION

Figure 1:
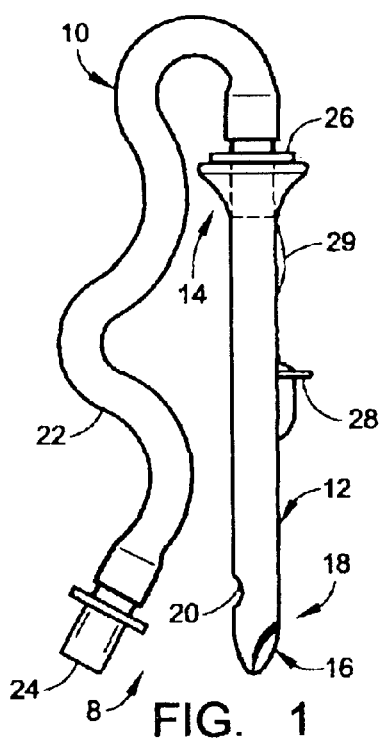
FIG. 1 is a perspective view of a rescue device, which is constructed in accordance with the present invention.
Figure 2:
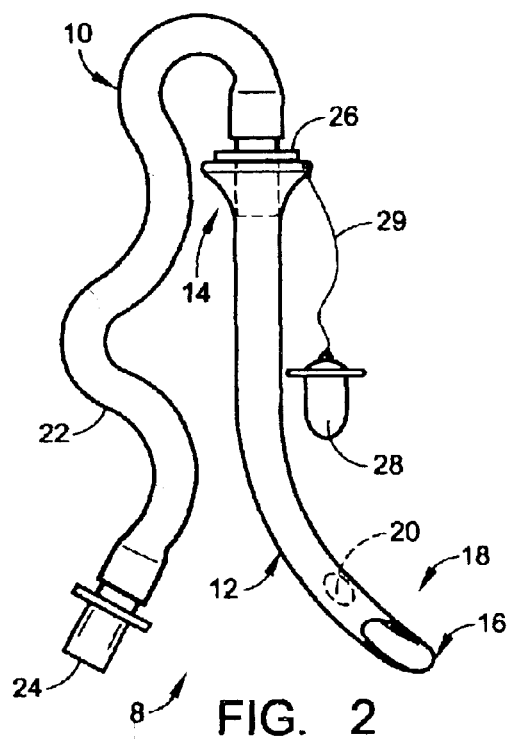
FIG. 2 is a side elevational view of the rescue device of FIG. 1 illustrating its bevel opening and the eye opening disposed slightly proximal to the bevel shaped opening.

Referring now to the drawings and more particularly to FIGS. 1–2, thereof there is illustrated a rescue device 8, which is constructed in accordance with one preferred embodiment of the present invention. The rescue device 8 is utilized to ventilate a patient when other conventional non-surgical methods of ventilation are ineffective.

Considering now the rescue device 8 in greater detail with reference to FIGS. 1–2, the rescue device 8 generally comprises an air delivery assembly 10 and a single-lumen nasopharyngeal airway or trumpet 12 having a flared flanged proximal end 14 and a bevel shaped opening 16 at its distal end 18. A small eye or opening 20 is disposed slightly proximal to the beveled shaped opening 16. The eye 20 in cooperation with the bevel opening 16 helps distribute positive pressure air into the airway of a patient and thus, helps prevent the trumpet 12 from being dislodged from the nostril of the patient due to excessive pressure buildup in the airway of the patient. In this manner the delivery of the positive pressure air into the airway of the patient causes the periglottic area within the airway to expand or distend and causes the larynx to open, thus facilitating the pulmonary exchange of air.

The air delivery assembly 10 generally includes an elongated tube 22 having an endotracheal tube connector 24 at its proximal end and trumpet connector 26 at its distal end. A nose plug 28 is secured by an extension 29 slightly spaced from the distal end of the tube 22. The endotracheal tube connector 24 is adapted to be quickly and easily wedged into an air delivery device, such as an airbag 30, as best seen in FIG. 3C. The trumpet connector 26 is adapted to be quickly and easily wedged into the flared flanged proximal end 14 of the trumpet 12 as best seen in FIGS. 1–2.

Figure 3A:
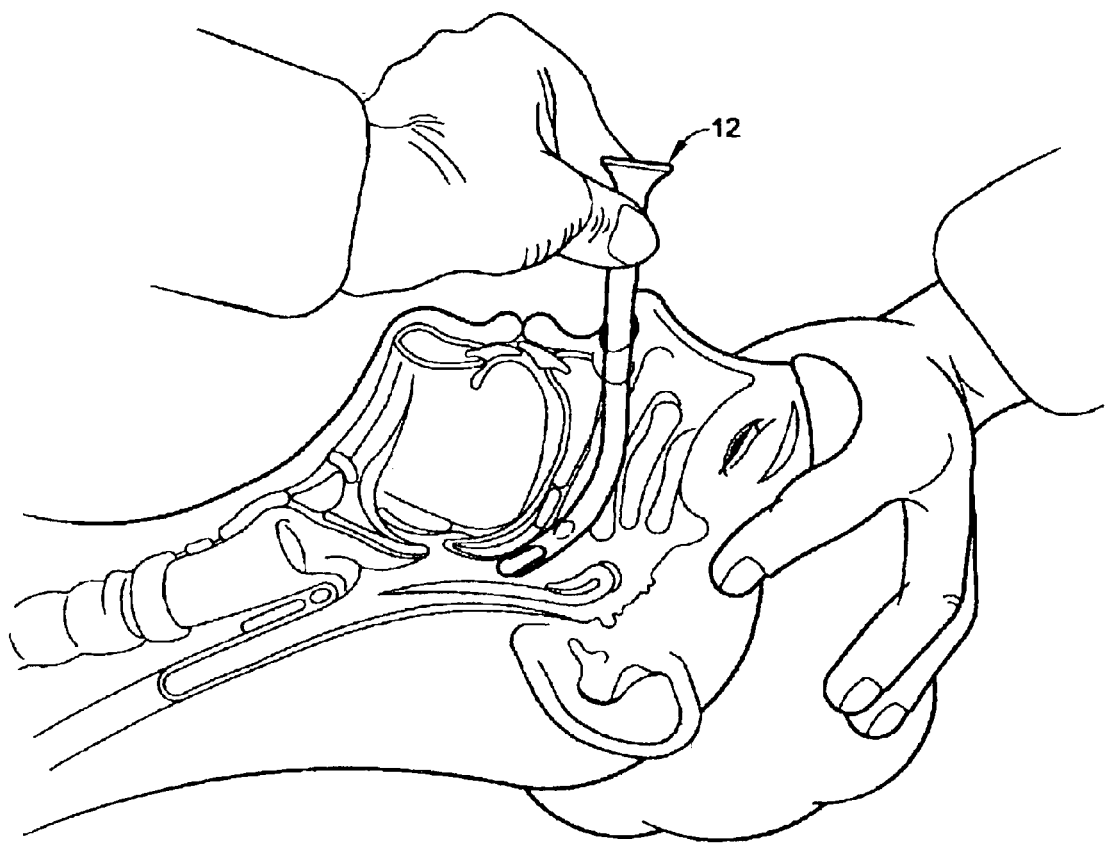
FIG. 3A illustrates the step of positioning a patient for the proper insertion of the rescue device into a single nostril of the patient.
Figure 3B:
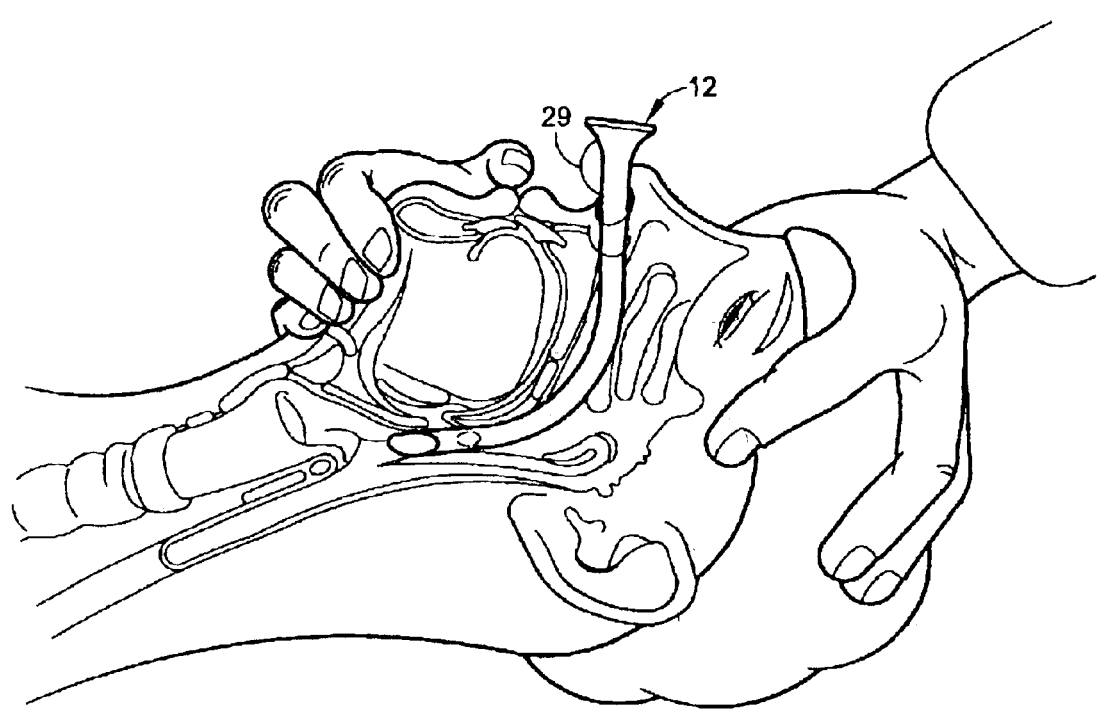
FIG. 3B illustrates the step of inserting the rescue device into the nostril of the patient for passage to the seriglottic space within the airway of the patient.
Figure 3C:
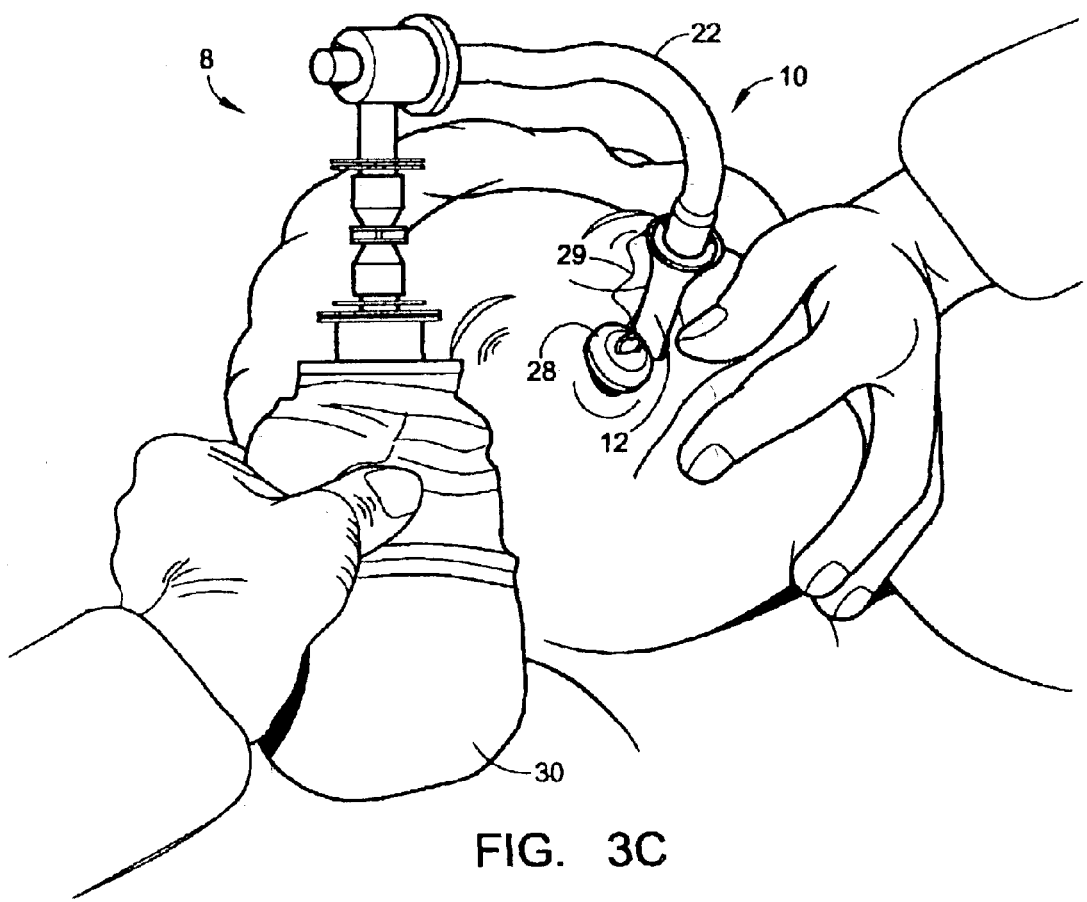
FIG. 3C illustrates the step of the patient being ventilated using the rescue device of FIG. 1.

Considering now the method of using the rescue device 8 with reference to FIGS. 3A–3C, the patient is placed in a face up prone position with the head slightly back to make certain the airway of the patient is open. The rescue device 8 is then lubricated and inserted by its distal end 18 into a single nostril of a distressed patient and pushed downward a sufficient distance until the distal end 18 is positioned within the periglottic airway space of the patient. Next the airbag 30 is attached to the endotracheal tube connector 24. The trumpet connector 26 is then wedged into the flared flanged proximal end 14 of the trumpet 12. The medical practitioner then inserts the nose plug 28 into the open nostril of the patient to close the nasal passageway at one end. The medical practitioner then squeezes the airbag 30 to discharge a wave of air into the nasal passageway and lungs of the patient. The mouth of the patient may be held shut during the squeezing action and then allowed to open during the exhaling of the air. The delivery of the positive pressure air causes the periglottic space to expand as well as opening the larynx to facilitate pulmonary exchange of air. The medical practitioner can then squeeze the airbag 30 in synchronization with the inspiratory phase allowing sufficient time for exhalation by the patient. It should be noted that the extension tube 22 as best seen in FIG. 3C, permits the airbag 30 to be spaced from the face of the medical patient and thus allows greater freedom for the medical practitioner and less discomfort for the patient.

Although in the preferred embodiment of the present invention, the nose plug 28 is described as being attached to the nasal trumpet 12 at about its flared flanged end, 14, it is contemplated that the nose plug 28 may be a separate or loose component which is not secured by an extension to the nasal tube trumpet 12.

Figure 5:
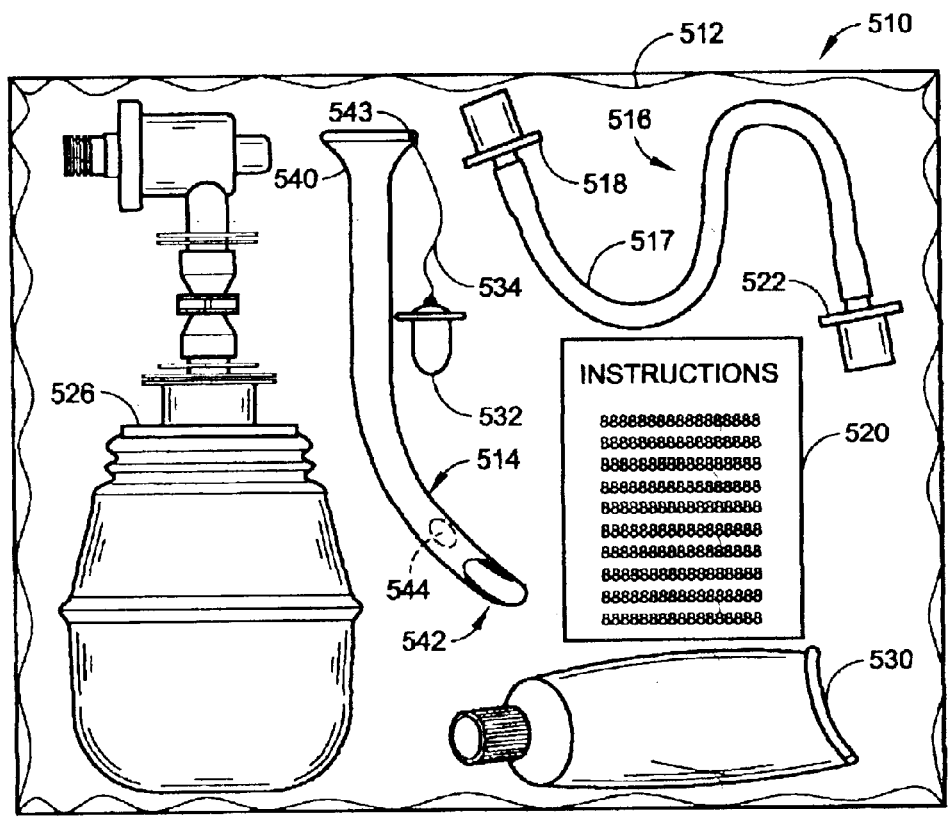
FIG. 5 is a pictorial view, illustrating operative elements of another ventilation kit, which is constructed in accordance with the present invention.

Referring now to the drawings and more FIG. 5 thereof, there is illustrated a ventilation rescue kit 510, which is constructed in accordance with another preferred embodiment of the present invention. The ventilation rescue kit 510 is utilized to ventilate a medical patient.

Considering now the ventilation rescue kit 510 in greater detail with reference to FIG. 5, the rescue kit 510 generally includes a storage container in the form of a clear plastic bag 512 that holds all the operative elements of the kit for easy in access and storage. In this regard, the bag 512 has a sufficient internal volume to hold the operative elements which include an airway or trumpet 514; a coupler 516; a set of instructions 520; an airbag 526; a container of lubricant 530; and a nostril plug 532 that is secured by an extension 534 slightly distal to the proximal end of the airway 514.

Considering now the ventilation kit 510 in still greater detail, the airway 514 is a single-lumen nasopharyngeal airway such as a 24 to 38 French soft nasal airway having a flared proximal end 540 and a wedge shape distal end 542. A small eye opening 544, commonly called a "Murphy eye" is disposed near the distal end 542 and functions to reduce the need to change nostrils.

Considering now the coupler 516 in greater detail with reference to FIG. 5, the coupler 516 is an elongated hollow tube 517 having a trumpet connector 518 disposed at its distal end 520 and an air delivery connector 522 disposed at its proximal end 524. The trumpet connector 518 and the air delivery connector 522 are both endotracheal tube connectors to permit one of them, to be easily and quickly connected to the air bag 526 and to permit the other one of them, the trumpet connector 518 to be easily and quickly wedged into the proximal end of the nasal trumpet 514.

Although in the preferred second preferred embodiment of the present invention the trumpet connector 518 is described as being wedged in the distal end of the extension tube 517 it is contemplated that the trumpet connector could be an endotracheal tube connector that is wedged in the proximal end opening of the trumpet 514. In this manner the distal end of the extension tube would simply be pushed onto the endotracheal tube connector extending out of the proximal end of the nasal trumpet.

The flared proximal end 540 includes a generally circular flange 541 having a small hole 543 disposed near its outer perimeter. The extension 534 is secured by one of its ends within the hole 543 and is secured to the nose plug 532 at the other one of its ends. In this manner, the nose plug 532 is secured slightly spaced from the proximal end 534 of the nasal trumpet 514 for immediate use by the medical practitioner once the nasal trumpet 514 has been lubricated and inserted within the nostril of a patient for air delivery purposes. More particularly, the extension 524 is sufficiently long to permit the nose plug 532 to be inserted into an open nostril of the patient (as best seen in FIG. 3C) when the nasal trumpet 514 is inserted into the other nostril of the patient.

In use, a medical practitioner opens the bag 512 and assembles the rescue kit 510 by attaching the airbag 526 to the endotracheal connector 522 and then attaching the trumpet connector 518 to the flared proximal end of the trumpet 514. As noted earlier, attaching the connector 518 to the trumpet 514 is easily accomplished by wedging the connector 518 into the proximal end opening of the trumpet 514.

To facilitate ease of inserting the trumpet 514 into the nostril of the medical patient and down into the airway of the patient, the medical practitioner opens the lubricant container 530 and applies the lubricant over the outer surface area of the trumpet 514. The trumpet 514 is then inserted into one of the nostrils of the medical patient and downward into the airway passage of the patient a sufficient distance to bring the flared proximal end of the trumpet 514 in close proximity to the nostril passage opening as best seen in FIGS. 3B–C.

The medical practitioner then inserts the nose or nostril plug 532 into the open or other nostril of the patient to help establish a positive pressure airway environment. In this regard, once the other nostril of the patient has been occluded, the medical practitioner can immediately begin squeezing the airbag 526 to deliver positive pressure air into the airway of the patient. When the airbag 526 is released, the exhaling action of the patient occurs through the open mouth of the patient. After the patient has exhaled, the airbag 526 can once again be squeezed to discharge another wave of positive pressure air into the lungs of the patient. This process is repeated until there is a satisfactory pulmonary exchange of air. If need be, a respirator or ventilator (not shown) may be attached to the proximal end of the extension tube 516 to provide for assisted breathing.

Figure 4:
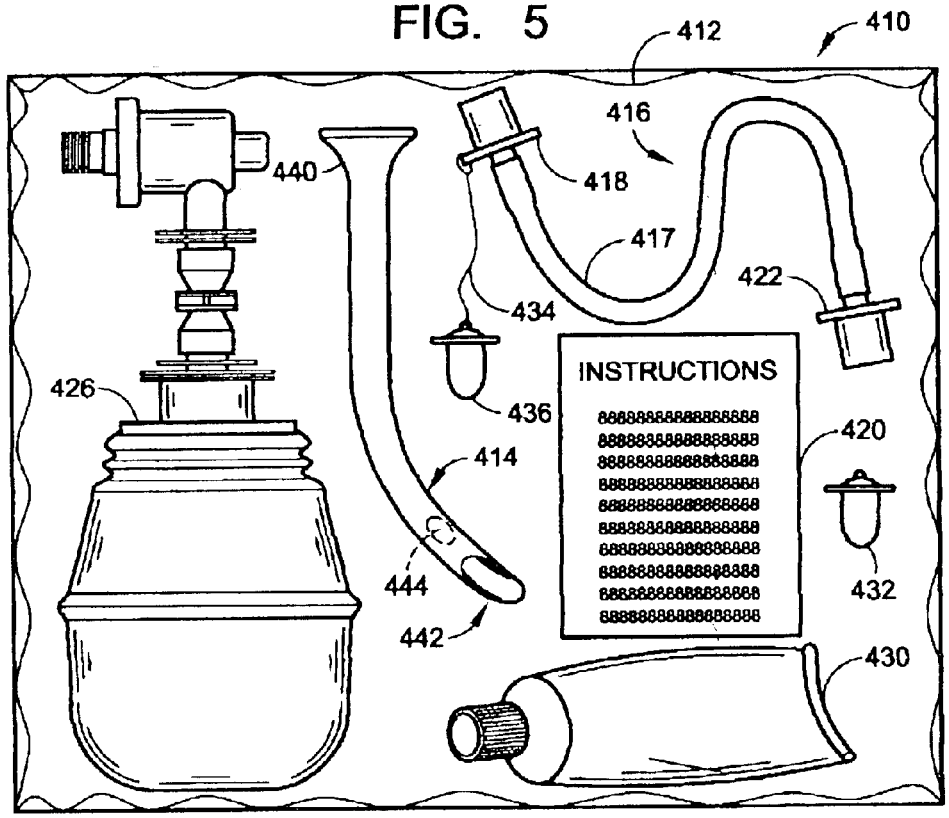
FIG. 4 is a pictorial view, illustrating operative elements of a ventilation kit, which is constructed in accordance with the present invention.

Referring now to the drawings and more FIG. 4 thereof there is illustrated another ventilation rescue kit 410, which is constructed in accordance with another preferred embodiment of the present invention. The ventilation rescue kit 410 is utilized to ventilate a medical patient.

Considering now the ventilation rescue kit 410 in greater detail with reference to FIG. 4, the rescue kit 410 generally includes a storage container in the form of a clear plastic bag 412 that holds all the operative elements of the kit for easy in access and storage. In this regard, the bag 412 has a sufficient internal volume to hold the operative elements, which include an airway or trumpet 414; a coupler 416; a set of instructions 420; an airbag 426; a container of lubricant 430; and a nostril plug 432.

Considering now the ventilation kit 410 in still greater detail, the airway 414 is a single-lumen nasopharyngeal airway such as a 24 to 38 French soft nasal airway having a flared proximal end 440 and a wedge shape distal end 442. A small eye opening 444, commonly called a "Murphy eye" is disposed near the distal end 442 and functions to reduce the need to change nostrils.

Considering now the coupler 416 in greater detail with reference to FIG. 4, the coupler 416 is an elongated hollow tube 417 having a trumpet connector 418 disposed at its distal end 420 and an air delivery connector 422 disposed at its proximal end 524. The trumpet connector 418 and the air delivery connector 422 are both endotracheal tube connectors.

An extension 434 is secured to the outer wall of the coupler 414 by one of its ends adjacent to the trumpet connector 418 and is secured to a nose plug 436 at the other one of its ends. In this manner, the nose plug 436 is secured slightly spaced from the proximal end 434 of the nasal trumpet 414 for immediate use by the medical practitioner once the nasal trumpet 514 has been connected to the coupler 416, lubricated and inserted within the nostril of a patient for air delivery purposes. More particularly, the extension 424 is sufficiently long to permit the nose plug 436 to be inserted into an open nostril of the patient when the nasal trumpet 414 is inserted into the other nostril of the patient and connected to the air bag 426 via the coupler 416.

The method of using the kit 410 is substantially similar to the method of using the kit 510 and therefore the method will not be described hereinafter in greater detail. It should be noted however, that nose plug 532, which is packaged separate and loose is the primary nose plug for use in the method of ventilating the patient. In this regard, nose plug 536, which is attached to the coupler 516, is a backup nose plug in the event nose plug 536 should be misplaced during the ventilation procedure.

Figure 6:
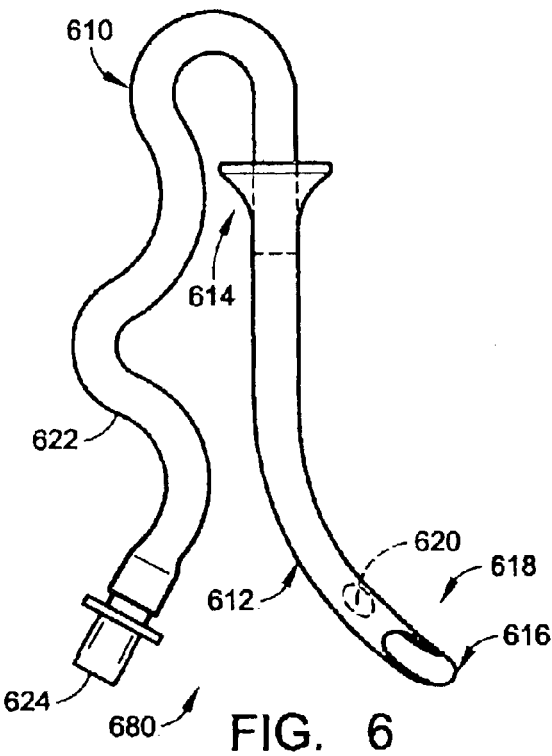
FIG. 6 is a perspective view of a rescue device, which is constructed in accordance with the present invention.

Referring now to the drawings and more particularly to FIG. 6, thereof there is illustrated a rescue device 608, which is constructed in accordance with another preferred embodiment of the present invention. The rescue device 6088 is utilized to ventilate a patient when other conventional non-surgical methods of ventilation are ineffective.

Considering now the rescue device 608 in greater detail with reference to FIG. 6, the rescue device 608 generally comprises an air delivery assembly 610 that includes a single-lumen nasopharyngeal airway or trumpet 612 having a flared flanged proximal end 614 and a bevel shaped opening 616 at its distal end 618. A small eye or opening 620 is disposed slightly proximal to the beveled shaped opening 616. The eye 620 in cooperation with the bevel opening 616 helps distribute positive pressure air into the airway of a patient and thus, helps prevent the trumpet 612 from being dislodged from the nostril of the patient due to excessive pressure buildup in the airway of the patient. In this manner the delivery of the positive pressure air into the airway of the patient causes the periglottic area within the airway to expand or distend and causes the larynx to open, thus facilitating the pulmonary exchange of air.

Figure 7:
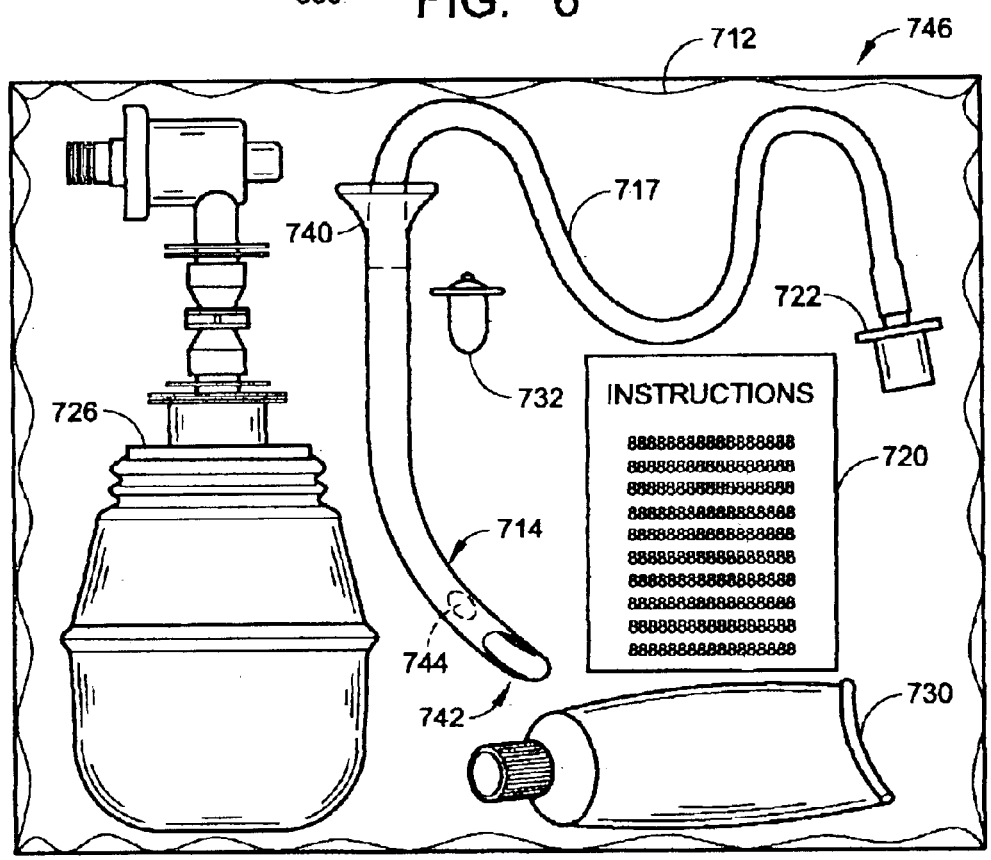
FIG. 7 is a pictorial view, illustrating operative elements of still yet another ventilation kit, which is constructed in accordance with the present invention.

The air delivery assembly 610 further includes an elongated tube 622 having an endotracheal tube connector 624 at its proximal end and a sufficiently small outer diameter to be received within the airway passage opening at the flared proximal end 614 of the nasal trumpet 612. The endotracheal tube connector 624 is adapted to be quickly and easily wedged into an air delivery device, such as an airbag 726, as best seen in FIG. 7. The tube 622 is composed of a material that interacts in a friction like manner with the interior wall structure of the nasal trumpet 612. That is, when the distal end of the extension tube 622 is inserted into the proximal end opening of the nasal trumpet 612, the tube 622 and the nasal trumpet interact with one another such that the tube 622 cannot be removed or separated from the nasal trumpet 612.

The extension tube 622 is sufficiently soft and pliable to form an inner cushioning wall within the interior proximal end of the trumpet 612. That is the distal end of the extension tube 622 secured within the nasal trumpet 612 cooperates with the flared proximal end 614 of the nasal trumpet to provide a soft non-tissue irritating nose plug when the nasal trumpet 612 is fully inserted into a nostril opening of a patient. These are important features of the present invention because the endotracheal tube connector 624 at the proximal end of the extension tube 622 is adapted to be connected in a fast convenient manner to an air delivery device, such as the air bag 726, while the extension tube 622 has a sufficient length to space the air delivery device from the face of the patient thereby facilitating both patient comfort and easy in operating the air delivery device when it is attached at the proximal end of the air delivery extension-tube.

The method of using the rescue device 608 is similar to the method of using the rescue device 8. That is, a patient is placed in a face up prone position with the head slightly back to make certain the airway of the patient is open. The rescue device 608 is then lubricated using a lubricant conveniently provided in a tube 730. The lubricated rescue device 608 is then inserted by its distal end 618 into a single nostril of a distressed patient and pushed downward a sufficient distance until the distal end 618 is positioned within the periglottic airway space of the patient. Next the airbag 726 is attached to the endotracheal tube connector 624. The medical practitioner then inserts a nose plug, such as the nose plug 732, into the open nostril of the patient to close the nasal passageway at one end. The medical practitioner then squeezes the airbag 726 to discharge a wave of air into the nasal passageway and lungs of the patient. The mouth of the patient may be held shut during the squeezing action and then allowed to open during the exhaling of the air. The delivery of the positive pressure air causes the periglottic space to expand as well as opening the larynx to facilitate pulmonary exchange of air. The medical practitioner can then squeeze the airbag 726 in synchronization with the inspiratory phase allowing sufficient time for exhalation by the patient. It should be noted that the extension tube 622 permits the airbag 626 to be spaced from the face of the patient and thus allows greater freedom for the medical practitioner and less discomfort for the patient.

Referring now to the drawings and more FIG. 7 thereof, there is illustrated a ventilation rescue kit 710, which is constructed in accordance with another preferred embodiment of the present invention the ventilation rescue kit 710 is utilized to ventilate a medical patient.

Considering now the ventilation rescue kit 710 in greater detail with reference to FIG. 7, the rescue kit 710 generally includes a storage container in the form of a clear plastic bag 712 that holds all the operative elements of the kit for easy in access and storage. In this regard, the bag 712 has a sufficient internal volume to hold the operative elements, which include an air delivery assembly 714; a set of instructions 720; an airbag 726; a container of lubricant 730; and a nostril plug. The air delivery assembly 714 is substantially similar to the air delivery assembly 608 and will not be described hereinafter in greater detail.

In use, a medical practitioner opens the bag 712 and removes its contents. Next the medical practitioner using the air delivery assembly 714 proceeds ventilating a patient by first lubricating the air delivery assembly nasal trumpet, inserting the trumpet by its distal bevel end into a single nostril of a distressed patient until the distal end occupies the periglottic space of the patient; attaching the air bag 726 to the proximal end of the extension tube and then occluding the other nostril of the patient with the nose plug. With the nasal trumpet so positioned the medical practitioner applies positive pressure to the air bag 726 to distend the periglottic space of the patient and open the larynx thereby facilitating pulmonary exchange of air. The squeezing of the air bag is repeated in synchronization with the inspiratory phase allowing sufficient time for exhalation through the mouth of the patient.

While a particular embodiment of the present invention has been disclosed, it is to be understood that various different modifications are possible and are contemplated within the true spirit and scope of the appended claims. There is no intention, therefore, of limitations to the exact abstract or disclosure herein presented.

We claim:

1. A rescue device, comprising:
   a single-lumen nasopharyngeal trumpet extending between a proximal end and a distal end for insertion into a nasal passageway;
   a beveled distal end on said trumpet forming a tip on said trumpet; a flared proximal end on said trumpet, said flared proximal end terminating in a circular flange with a centrally disposed opening;
   an extension tube having an endotracheal tube connector secured at its proximal end and a trumpet connector secured at its distal end, said endotracheal tube connector being adapted to be secured to an airbag and said trumpet connector being secured within said centrally disposed opening; and
   an extension secured by one of its ends to said extension tube slightly spaced from said trumpet connector and having a nose plug secured at another one of its ends.

2. The rescue device according to claim 1, wherein said single-lumen nasopharyngeal trumpet is between about 24 millimeters and about 38 millimeters in length.

3. The rescue device according to claim 2 wherein said trumpet has a more preferred length of between about 28 millimeters and about 34 millimeters.

4. The rescue device according to claim 3 wherein said trumpet has a most preferred length of between about 30 millimeters and about 32 millimeters.

5. The rescue device according to claim 2, wherein said trumpet connector is between about 7.5 millimeters and about 8.0 millimeters in diameter at both its distal end and its proximal end.

6. A rescue device, comprising:
   a single-lumen nasopharyngeal trumpet extending between a proximal end and a distal end for insertion into a nasal passageway;
   a beveled distal end on said trumpet forming a tip on said trumpet; a flared proximal end on said trumpet, said flared proximal and terminating in a circular flange with a centrally disposed opening;
   an extension tube having an endotracheal tube connector secured at its proximal end and a trumpet connector secured at its distal end, said endotracheal tube connector being adapted to be secured to an airbag and said trumpet connector being secured within said centrally disposed opening;
   wherein said circular flange has an opening adjacent to its outer periphery, said opening having secured therein an elongated extension; and
   wherein said extension includes a nose plug secured at its distal end.

7. A method of ventilating a medical patient, comprising the steps of:
   providing a single-lumen nasopharyngeal trumpet having a flared proximal end and a bevel distal end opening;
   providing an extension tube having an endotracheal tube connector attached at its proximal end and a trumpet connector attached at its distal end;
   inserting said single-lumen nasopharyngeal trumpet into one nostril of the medical patient a sufficient distance to position said bevel distal end opening in the periglottic space adjacent to the posterior portion of a patient's trachea;
   attaching an air delivery device to said endotracheal tube connector;
   attaching said trumpet connector to said trumpet;
   delivering air under pressure from said air delivery device to said trumpet to facilitate the pulmonary exchange of air within the lungs of the medical patient;
   wherein the step of providing a trumpet includes providing an eye opening in said single-lumen nasopharyngeal trumpet slightly proximal to said bevel distal end opening;
   wherein said step of attaching an air delivery device to said endotracheal tube connector includes providing an airbag;
   occluding the other nostril of the medical patient with a nose plug; and
   wherein said step of delivering air under pressure includes the step of squeezing said airbag to discharge a wave of air therefrom.

8. The method of claim 7, further comprising the step of:
   holding the mouth and lips of the medical patient tightly shut during said step of squeezing.

9. A ventilation kit, comprising:
   a nasopharyngeal airway having a flared proximal end and a beveled distal end;
   an air delivery device for providing air under pressure;
   a coupler for securing said nasopharyngeal airway to said air delivery device;
   a container of lubricant;
   a container for storing said airway, said air delivery device and said container of lubricant for easy access;
   wherein said nasopharyngeal airway includes an eye opening slightly proximal to said beveled distal end;
   wherein said coupler is an extension tube having an endotracheal tube connector extending from its distal end;
   wherein said endotracheal tube connector is adapted to be wedged into the proximal end of said nasopharyngeal airway;
   wherein said air delivery device is a hand operated air bag;
   wherein said nasopharyngeal airway is a single-lumen airway;
   an extension having a proximal end and a distal end, said proximal end being secured to the proximal end of said airway; and
   a nose plug secured at the distal end of said extension;
   whereby said extension is sufficiently long to permit said nose plug to be inserted into an open nostril of a patient when said airway is inserted into another open nostril of a patient.

10. The kit according to claim 9 wherein said coupler is an extension tube.

11. The kit according to claim 10, wherein said extension tube includes a pair of endotracheal tube connectors wedged in said tube spaced from one another and mounted in opposite orientations to one another to permit one of said endotracheal tube connectors to be wedged within said airway and to permit the other one of said endotracheal tube connectors to be secured to said air delivery device.

12. The kit according to claim 11, wherein said coupler further includes:

a nose plug secured by an extension to an outer wall of said extension tube;

said extension being sufficiently long to permit said nose plug to be inserted into an open nostril of a patient when said airway is inserted into another open nostril of the patient.

13. A rescue device, comprising:

a single-lumen nasopharyngeal trumpet extending between a proximal end and a distal end for insertion into a nasal passageway;

a beveled distal end on said trumpet forming a tip on said trumpet;

a flared proximal end on said trumpet, said flared proximal end terminating in a circular flange with a centrally disposed opening;

said opening having disposed therein an extension tube having an endotracheal tube connector secured at its proximal end, said endotracheal tube connector being adapted to be secured to an air bag; and said extension tube cooperating with said flared proximal end to provide a soft non-tissue irritating nose plug when the nasal trumpet is fully inserted into a nostril opening of the patient.

14. A ventilation kit, comprising:

a single single-lumen nasopharyngeal trumpet extending between a proximal end and a distal end for insertion into a nasal passageway;

a beveled distal end on said trumpet forming an open ended tip on said trumpet;

a flared proximal end on said trumpet, said flared proximal end terminating in a circular flange with an opening disposed therein; and wherein said nasopharyngeal trumpet includes an eye opening slightly proximal to said beveled distal end an air delivery for providing air under pressure to said trumpet; said extension tube includes a pair of endotracheal tube connectors mounted in opposite orientations to one another in said tube to permit one of said endotracheal tube connectors to be wedged within said single-lumen nasopharyngeal trumpet and to permit the other one of said enottracheal tube connectors to be secured to said air delivery device; a nose plug secured slightly distal to the proximal end of said single-lumen nasopharyngeal treumpet; and attachment means coupled to said nose plug to permit it to be spaced a sufficient distance from said single-lumen nasopharyngeal trumpet to permit the nose plug to be inserted into a nostril of a patient.

15. The ventilation kit according to claim 14, further comprising:

an extension tube disposed in the flange opening.

16. The ventilation kit according to claim 15, wherein said extension tube includes an endotracheal tube connector secured at its proximal end, said extension tube cooperating with said flared proximal end to provide a soft non-tissue irritating nose plug when the nasal trumpet is fully inserted into a nostril opening of a patient.

17. The ventilation kit according to claim 14, further comprising:

a container of lubricant; and a container for storing said single-lumen nasopharyngeal trumpet, said air delivery device, said nose plug and said container of lubricant for easy access.

* * * * *